May 26, 1942. T. J. MORRIS Plant Pat. 523

ROSE PLANT

Filed Nov. 18, 1941

INVENTOR
T. J. MORRIS
BY
Robb & Robb
ATTORNEYS

Patented May 26, 1942

Plant Pat. 523

UNITED STATES PATENT OFFICE

523

ROSE PLANT

Theodore J. Morris, San Fernando, Calif., assignor to Armstrong Nurseries, Inc., Ontario, Calif., a corporation of California Application November 18, 1941, Serial No. 419,643

1 Claim. (Cl. 47—61)

The present discovery relates to a new and distinct variety of rose plant, originating as a bud sport of the bush rose "Charlotte Armstrong," and discovered by me growing upon its parent bush in a field of "Charlotte Armstrong" plants.

Because of its greater height of growth than the parent variety, the value of this mutation was easily recognized. I, therefore, proceeded with its development and propagation.

Careful study of this new variety discloses that it distinguishes from its parent in several major features, namely, its vigorous growing habit, characterized by its strong canes attaining a height of twelve to fourteen feet or more as distinguished from the usual height of three or four feet of the bush form of the rose, "Charlotte Armstrong"; its habit of producing many more flowers in the spring than can be found at any one time on the parent variety; and its intermittent flowering during the remainder of the season.

Of no less importance is the fact that the flowers of this new rose variety are usually larger in size and greater in petalage than the flowers found on the parent bush variety, there being from seven to twelve more petals, thus averaging from thirty-five to forty-five petals, which characteristic in flowers of a climber lends to it particular value from the standpoint of attractive display.

Figure 1:
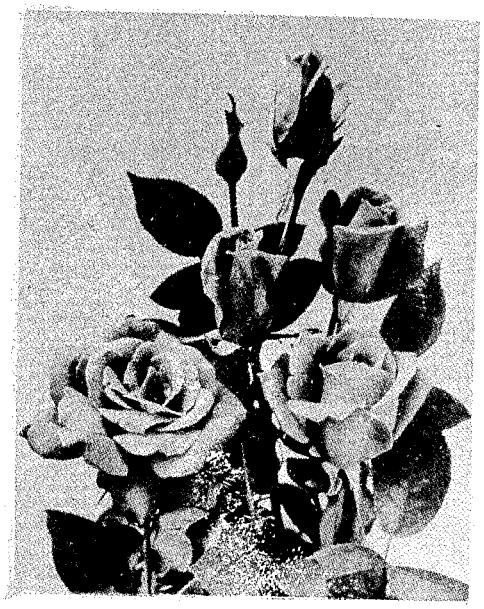
Figure 2:
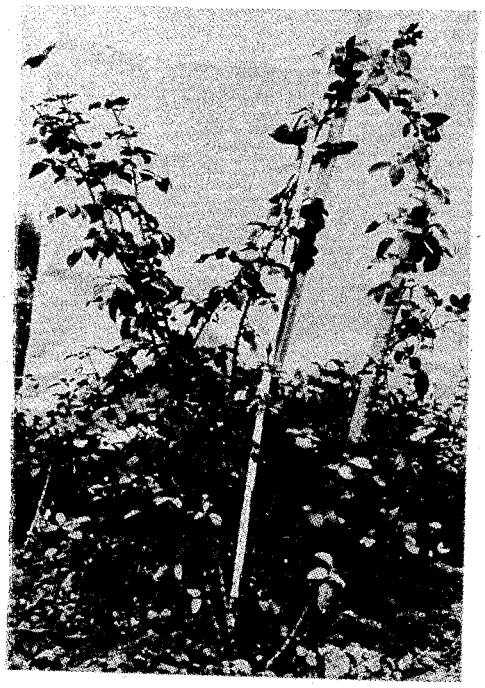

In all other respects it is like its parent variety, including the color of the bud or blossom, and since said parent variety is fully disclosed in the prior Plant Patent No. 455, dated February 25, 1941, and granted to Walter E. Lammerts therefor, detailed description of the plant is not given herein. However, the accompanying drawing shows in Figure 1 a specimen of the flowers of this new variety, and in Figure 2 is illustrated a year's growth of a specimen of the new rose in association with a yardstick to indicate its vigorous climbing growth.

The new variety has been asexually reproduced by budding and grafting over a period of time, and the characteristics above referred to have proved to be permanently fixed.

I claim:

A new and distinct variety of rose plant of the climbing class, characterized as to novelty by its vigorous growing habit to unusual height, its production of greater number of flowers than found on its parent variety at any one time, its habit of intermittent flowering throughout the growing season, and the greater number of petals per flower than found on its parent variety, substantially as shown and described.

THEODORE J. MORRIS.